United States Patent
Miljanic et al.

(10) Patent No.: US 10,117,935 B2
(45) Date of Patent: Nov. 6, 2018

(54) ADSORPTION OF FLUORINATED ANESTHETICS WITHIN THE PORES OF MOLECULAR CRYSTALS

(71) Applicant: University of Houston System, Houston, TX (US)

(72) Inventors: Ognjen Miljanic, Houston, TX (US); Teng-Hao Chen, Houston, TX (US); Watchareeya Kaveevivitchai, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 15/534,923

(22) PCT Filed: Dec. 10, 2015

(86) PCT No.: PCT/US2015/065009
§ 371 (c)(1),
(2) Date: Jun. 9, 2017

(87) PCT Pub. No.: WO2016/094663
PCT Pub. Date: Jun. 16, 2016

(65) Prior Publication Data
US 2017/0368178 A1    Dec. 28, 2017

Related U.S. Application Data

(60) Provisional application No. 62/090,494, filed on Dec. 11, 2014.

(51) Int. Cl.
*A61K 47/22* (2006.01)
*B01D 53/02* (2006.01)
*C07D 231/16* (2006.01)

(52) U.S. Cl.
CPC ............ *A61K 47/22* (2013.01); *B01D 53/02* (2013.01); *C07D 231/16* (2013.01); *B01D 2253/20* (2013.01); *B01D 2257/2066* (2013.01); *B01D 2259/4533* (2013.01); *H05K 999/99* (2013.01); *Y02P 20/154* (2015.11)

(58) Field of Classification Search
CPC .............................. A61K 47/22; C07D 231/16
USPC .......................................... 514/406; 548/365.1
See application file for complete search history.

(56) References Cited

U.S. PATENT DOCUMENTS

2011/0230678 A1    9/2011    Jung et al.
2013/0047849 A1    2/2013    Zhang et al.

OTHER PUBLICATIONS

Chawla et. al. Current Research & Information on Pharmaceutical Science, 2004, 5(1), pp. 9-12.*
Newman et. al.; Drug Discovery Today; 2003, 8(19) pp. 898-905.*
International Patent Application No. PCT/US2015/065009 International Search Report and Written Opinion dated Jun. 29, 2016 (11 pages).
Chen, Teng-Hao et al., "Thermally robust and porous noncovalent organic framework with high affinity for fluorocarbons and CFCs," Nature Communications, Oct. 13, 2014 (online), vol. 5, (8 internal pages).
Doyle, D. John et al., "Silica zeolite scavenging of exhaled isoflurance: a preliminary report," Canadian Journal of Anesthesia, 2002, vol. 49, No. 8, pp. 799-804.
Chen, Teng-Hao et al, "Adsorption of fluorinated anesthetics within the pores of a molecular crystal," Chemical Communication, Aug. 4, 2015 (online), vol. 51, No. 74, pp. 14096-14098.
European Patent Application No. 15866527.3 extended European search report dated Aug. 8, 2018 (8 pages).
Gargiulo N. et al., "A chromium-based metal organic framework as a potential high performance adsorbent for anaesthetic vapours," RSC Advances, vol. 4, No. 90, Sep. 29, 2014, pp. 49478-49484.

* cited by examiner

*Primary Examiner* — Jeffrey H Murray
(74) *Attorney, Agent, or Firm* — Conley Rose, P.C.

(57) ABSTRACT

A method of delivering or sequestering anesthetic agents by adsorption of such agents by porous partially fluorinated compounds which display high weight adsorption capacities.

11 Claims, 8 Drawing Sheets

ADSORPTION OF FLUORINATED ANESTHETICS WITHIN THE PORES OF MOLECULAR CRYSTALS

CROSS-REFERENCE TO RELATED APPLICATIONS

This application is a 35 U.S.C. § 371 national stage entry of PCT/US2015/065009, filed on Dec. 10, 2015, which claims priority to U.S. Provisional Patent Application 62/090,494 filed Dec. 11, 2014, both of which are incorporated by reference herein in their entireties for all purposes.

STATEMENT REGARDING FEDERALLY SPONSORED RESEARCH OR DEVELOPMENT

This invention was made with government support under Grant No. CHE-1151292 awarded by the National Science Foundation. The United States government has certain rights in the invention.

BACKGROUND

Field of the Disclosure

This disclosure generally relates to the use of a class of partially fluorinated porous materials which comprise porous molecular crystals to adsorb fluorinated anesthetics with high weight adsorption capacities. More particularly, the disclosure relates to the use of such porous molecular structures in the field of anesthesia, wherein the porous structures may be used to deliver anesthetic gases to a patient; and may be used to sequester anesthetic gases after the administration of the gases such as during a medical procedure or post-operatively.

Background of the Technology

Many anesthetics used in medicine are small and extensively fluorinated molecules. Sevoflurane is an example of such, and is used as an inhalation anesthetic for induction and maintenance of general anesthesia. However, sevoflurane is currently under review for potential neurotoxicity, especially relevant to administration in infants and children, and rare cases report that (akin to halothane hepatotoxicity) that low frequency liver injury may occur. As such there is an need for: not only a method of safely delivering anesthetic gases, but sequestering such gases post operatively, or should a subject react adversely to the anesthetic compound during a procedure.

Further, capture and release of fluorinated anesthetics is an important problem for a number of other reasons: they are expensive, and their recycling is economically beneficial; postoperative exposure of medical personnel to anesthetic vapors may also be harmful in the long term; their adsorption under well-defined conditions is useful in controlled-release devices; and finally, fluorinated anesthetics are potent greenhouse gases because anesthetics contribute about 0.03% to the global warming effect. Although this is a small contributory percentage, per unit of mass fluorinated anesthetics are damaging. Their tropospheric lifetimes are significant (from about 1.2 years for sevoflurane to about 10 years for desflurane), and their 20 year global warming potentials (GWP20) are hundreds of times higher than that of $CO_2$. Some fluorinated anesthetics are also damaging to the tropospheric ozone layer.

BRIEF SUMMARY OF THE DISCLOSURE

Herein disclosed are the use of non-covalent organic frameworks (nCOF) composed of a small organic molecule whose crystal structure contains large and empty pores in the method of absorbing, binding or sequestering anesthetic agents. These structures are held together by a combination of [N—H . . . N] hydrogen bonds between (for example in "Compound 1" which, as used herein means the compound of Formula 1 (FIG. 1)) its terminal pyrazole rings and [π . . . π] stacking between the electron-rich pyrazoles and electron-poor tetrafluorobenzenes. This synergistic arrangement makes these structures stable to at least 250° C. Their internal pores have accessible Brunauer-Emmett-Teller (BET) surface area of 1,159 $m^2$ $g^{-1}$. Crystals of this nCOF adsorb fluorinated ether-based anesthetics such as but not limited to: sevoflurane, enflurane, isoflurane, methoxyflurane, and desflurane, and also fluorinated hydrocarbon anesthetics such as halothane and its derivatives (See FIG. 2), as well as non-fluorinated compounds. Such molecules have high adsorption capacities in weight percent (defined as weight of the adsorbed analyte divided by weight of the nCOF material, and multiplied by 100%). They are soluble, lightweight (since they do not have metals), and completely indifferent to moisture. One embodiment of a non-covalent organic framework comprises a compound of:

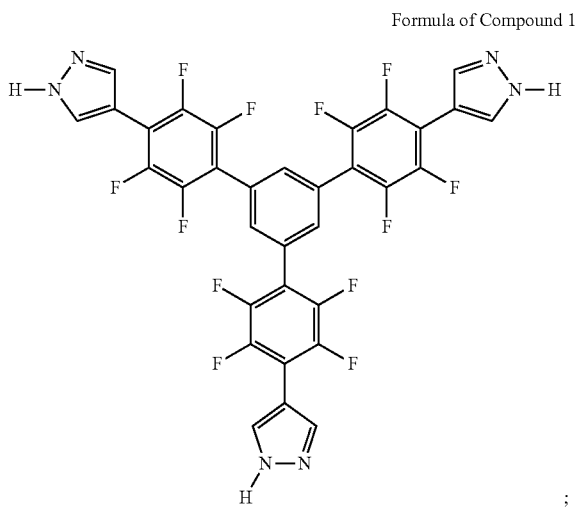 [SMILES: Fc1c(F)c(-c2cc(-c3c(F)c(F)c(-c4cn[nH]c4)c(F)c3F)cc(-c3c(F)c(F)c(-c4cn[nH]c4)c(F)c3F)c2)c(F)c(F)c1-c1cn[nH]c1]

Formula of Compound 1 wherein the compound forms a porous supramolecular structure; in another embodiment the non-covalent organic framework comprising the compound of formula 1, comprises at least one polymorph of the compound of formula 1; in a further embodiment a non-covalent organic framework comprising the compound of formula 1 comprises a mixture of polymorphs.

In one embodiment a method of binding an anesthetic agent is provided, wherein the method comprises contacting a gas comprising an anesthetic agent with a non-covalent organic framework comprising a compound of Formula 1; wherein the compound forms a porous supramolecular structure; and adsorbing said anesthetic agent within the pores of a compound of formula 1. In another embodiment the method further comprises delivering said anesthetic agent to a patient in need thereof. In some embodiments the method further comprises sequestering said anesthetic agent from a patient in need thereof, in one embodiment sequestering occurs post operatively, in a further embodiment sequestering occurs during an operative procedure. In one embodiment of the method described herein sequestering reduces toxicity, and in a further embodiment sequestering reduces post-operative stress. In one embodiment of the method herein described, the non-covalent organic framework comprises the compound of formula 1, wherein the compound comprises a polymorph or a mixture of polymorphs.

In another embodiment of the method described above, the framework has a weight adsorption capacity of about 50 to 75% for said anesthetic agent; in another embodiment of the method described above, the framework has a weight adsorption capacity of about 55 to 70%; and in a further embodiment the framework has a weight adsorption capacity of 60 to 65%.

In one embodiment a method of binding an anesthetic agent is provided, wherein the anesthetic agents comprise fluorinated anesthetics, non-fluorinated anesthetics or a combination thereof, and in a further embodiment the fluorinated anesthetics comprise: sevoflurane, enflurane, isoflurane, methoxyflurane, desflurane, halothane, or combinations thereof.

In another embodiment herein described, a method of binding an anesthetic gas is provided wherein the method comprises contacting a gas comprising an anesthetic agent with a non-covalent organic framework comprising a compound comprises a central ring, wherein the central ring is selected from a group comprising: 1,2,3,4,5,6-hexasubstituted benzene; a 1,2,4,5-tetrasubstituted benzene; a 1,3,5-trisubstituted or a 1,4-disubstituted benzene; wherein any of positions 1, 2, 3, 4, 5, and 6 may be substituted or unsubstituted, wherein, when said groups are substituted they comprise of alternating electron poor and electron rich groups or rings, wherein said electron-poor groups or rings comprise tetra-, tri-, or di-fluorobenzenes, oligocyanobenzenes, oligochlorobenzene, and wherein an electron-rich group of ring comprises benzene, pirydone, triazole, pyrazole, pyridine, and substituted benzenes; wherein the compound forms a porous supramolecular structure; and adsorbing said anesthetic agent within the pores of a the compound. In another embodiment the method further comprising delivering said anesthetic agent to a patient in need thereof, and in a still further embodiment the method comprises sequestering said anesthetic agent from a patient in need thereof.

A porous supramolecular structure comprising a covalent organic framework comprising a compound of Formula 1 is also disclosed herein. In some embodiments the structure comprises pores sizes of about 0.5 to about 2.5 nM. In a further embodiment the structure comprises pores sizes of about 1.6 nM, and in a further embodiment the pores sizes are chemically engineered. In some embodiments the supramolecular structure comprises a biosensor, and in some further embodiments the biosensor is recyclable.

DETAILED DESCRIPTION OF THE DISCLOSED EMBODIMENTS

Figure 1:
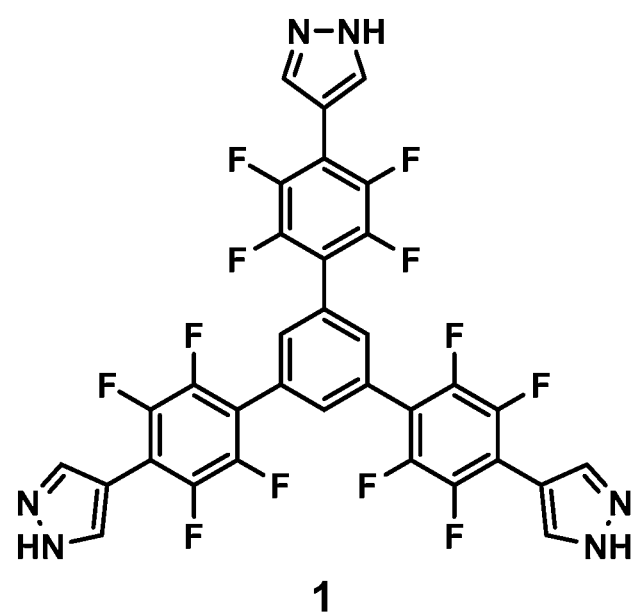
FIG. 1: the chemical structure of trispyrazole (compound of Formula 1) in accordance with an embodiment of this invention.

The following discussion is directed to various exemplary embodiments of the invention. One skilled in the art will understand that the following description has broad application, and the discussion of any embodiment is meant only to be exemplary of that embodiment, and not intended to intimate that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . " The term "substantially" generally means mostly, near completely, or approximately entirely. As used herein, the term "about," when used in conjunction with a percentage or other numerical amount, means plus or minus 10% of that percentage or other numerical amount. For example, the term "about 80%," would encompass 80% plus or minus 8%. Further, all publications and other references cited herein are incorporated in their entirety.

Adsorption of fluorinated anesthetics in porous materials have been studied previously: adsorption of enflurane and isoflurane were studied in soda lime, activated carbons, and zeolites; differential adsorption of enflurane enantiomers were used to separate them on a cyclodextrin-based gas chromatography column; Sevoflurane may be adsorbed at about 150 wt % within the pores of a crystalline metal-organic framework (MOF); halothane has been adsorbed on activated charcoal to levels of about 37 wt %, as well as on soda lime and even glass syringes; and Zeolites have also been used to adsorb desflurane.

Herein, it is disclosed that porous molecular crystals (of compound 1 for example) may bind fluorinated anesthetics as described herein up to a level of about 75 percent by weight. Porous molecular crystals are generally rare, and have not been previously explored as adsorbents in medicine. As such, they offer advantages over other adsorbents (e.g. zeolites or activated carbons as discussed above) because they are lightweight, do not contain potentially toxic metals, can be recycled, and their pore sizes can be specifically engineered. Further, the porous molecular structures of the prior art are hydrolytically sensitive, making them unsuitable for use in hospitals and environments where contact with moisture is likely. In contrast, compound 1 as disclosed herein, is both porous (with a surface area of 1159 $m^2\ g^{-1}$) and very robust. It is stable up to 250° C., and is unaffected by exposure to moisture, dilute acids and bases. Furthermore, adsorption of analytes within the pores of compound 1 for example, results in measurable changes in its UV/V is absorption properties, and therefore such a compound may be used as a sensor.

Many anesthetics used in medicine are small, and extensively fluorinated molecules. Therefore, because of their small size, fluorinated and hydrophobic character they both fit and bind well within the pores of compounds such as (1), which are lined with fluorine atoms. Compound (1) does not contain heavy metals, is light-weight and therefore shows high adsorption capacities in weight percent. Ether-based anesthetics such as but not limited to: sevoflurane, enflurane, isoflurane, methoxyflurane, and desflurane, as well as the extensively halogenated halothane are readily adsorbed into the porous structure of (1), and it's derivatives.

Compound (1) may be described as comprising a non-covalent organic framework (nCOF), which as detailed above are porous materials characterized by thermal stability, high porosities and modular synthesis as previously disclosed in U.S. Provisional patent application No. 61/994,482 (incorporated herein in its entirety by reference) and by Chen et al., "Thermally Robust and Porous Noncovalent Organic Framework with High Affinity for Fluorocarbons and Freons," *Nature Commun.* 2014, 5, DOI:10.1038/incomms/5131, also incorporated herein in its entirety by reference.

Therefore, disclosed herein in one embodiment is a method of adsorbing, binding or sequestering small molecules with a compound such as compound 1 that is exemplified by Formula 1 (trispyrazole (1), FIG. 1)) which organizes into a highly robust supramolecular structure with extrinsic high porosity through a combination of [π . . . π] stacking and hydrogen bonding therefore forming a nCOF. It is highly porous and has a high gas binding ability (Chen et al., "Adsorption of Fluorinated Anesthetics Within the Pores of a Molecular Crystal," *ChemComm.* 2015, 51, 14096-14098) herein in its entirety by reference In one embodiment, such compounds are constructed from a central core which can have linear, trigonal, tetragonal, or hexagonal geometry and 2-6 radially projecting arms which comprise fluorinated and electron-rich groups in an alternating arrangement. Pi-pi stacking between electron-rich and electron-poor nuclei in these arms creates the porous structure. Each molecule of 1 establishes short contacts with twelve of its neighbors: six [N—H . . . N] hydrogen bonds, which create a hexagonal two-dimensional lattice and six [π . . . π] stacking arrangements which propagate these layers into the third dimension.

In some embodiments a three-dimensional network results, with infinite one-dimensional channels protruding throughout the crystal; these channels are lined with fluorines and have a diameter of about 16.5 Å. These compounds can therefore, in some embodiments bind fluorinated anesthetics and in further embodiments bind non-fluorinated anesthetics, with varying and definable specificity.

In some embodiments the nCOF compounds described herein may be further modified while maintaining their porosity, high adsorption capacities and selectivity in the adsorption and sequestration of anesthetic molecules.

In some embodiments of method herein described, other compounds may be utilized, wherein for example in compound (1), the central benzene ring may be switched to a benzene derivative with a substitution pattern such that the compound can be used as adsorbents for anesthetic gases, wherein the rate of adsorption, and the selectivity of the compound for a specific anesthetic molecule cane be selectively modified or fine-tuned based on the specific substitution pattern of the derivative of compound (1). In another embodiment, the tetrafluorinated benzene rings in the structure of (1) can be switched to unsubstituted, in further embodiments other functional groups can be inserted between the central core and the tetrafluorinated benzene ring in the structure of (1). In still further embodiments, the pyrazole rings in the structure of (1) can be switched to any other carbocyclic or heterocyclic ring, and other functional groups can be inserted between the pyrazole and the tetrafluorinated benzene ring in the structure of (1).

EXAMPLES

Embodiments of the adsorption of fluorinated anesthetics within the pores of (1) were measured using thermogravimetric analysis, and are depicted in FIGS. 3-7. In each of these figures, horizontal axes plot time, while the vertical axes plot the weight change of the samples. The increase of weight is indicative of the adsorption of the analyte (in some embodiments fluorinated anesthetics) within the pores, and quantifies the amount of bound analyte.

Figure 2:
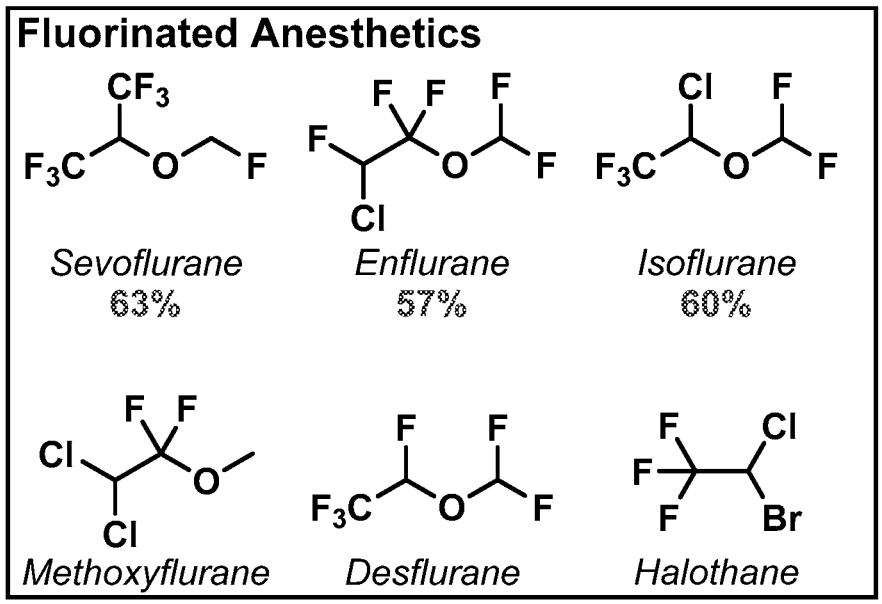
FIG. 2(A): depicts examples of anesthetics that bind within the pores of compounds exemplified by trispyrazole (1) in accordance with an embodiment of this invention.
FIG. 2(B): is a plot depicting a temperature program used during the thermogravimetric analysis (TGA)-bases measurements of adsorption of enflurane; isoflurane; sevoflurane; methoxyflurane; and halothane, within the pores of a trispyrazole assembled into a macromolecular porous structure in accordance with an embodiment of this invention.
Figure 2:
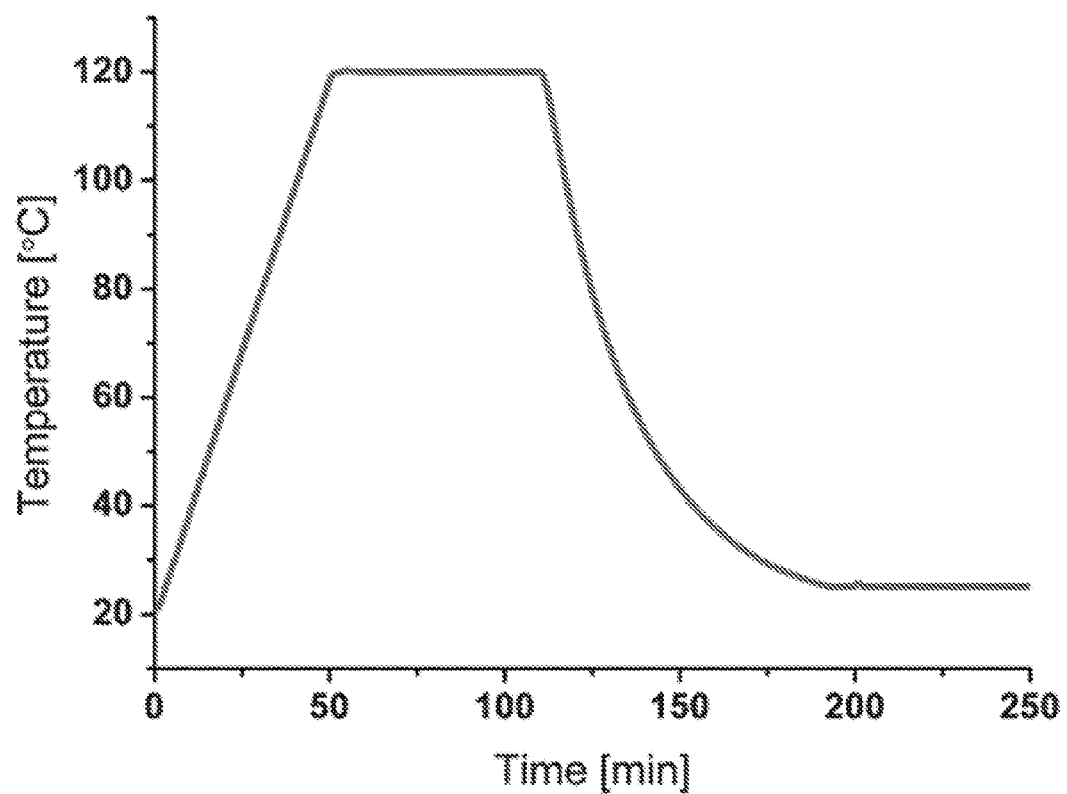
Figure 3:
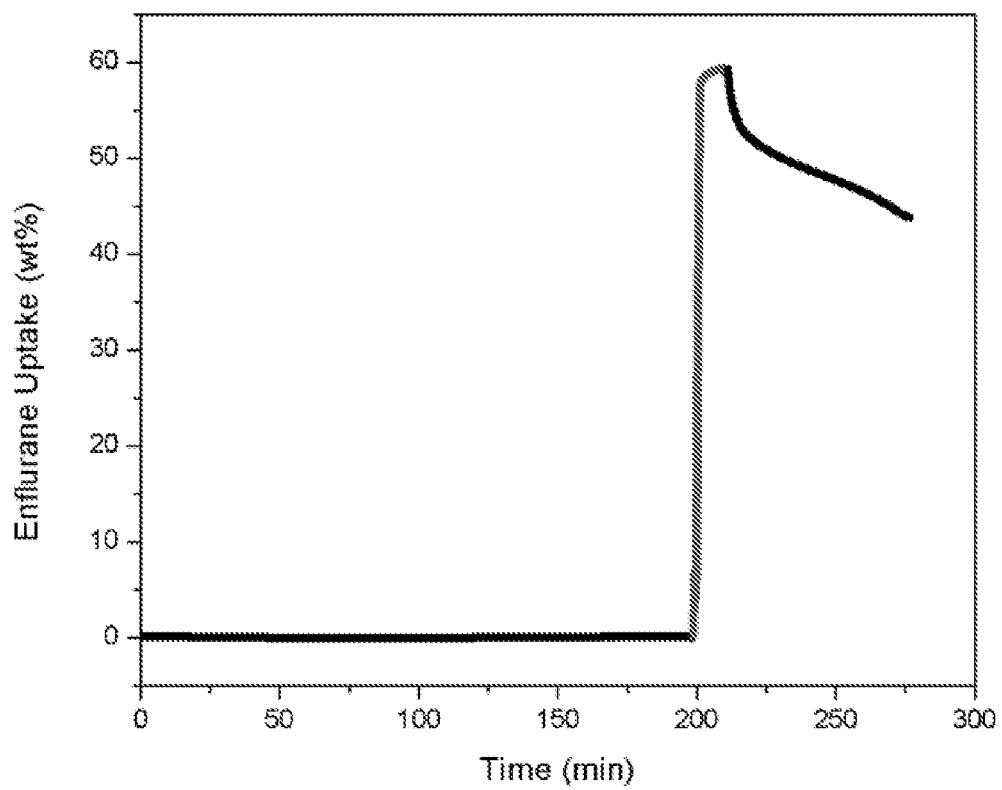
FIG. 3: is a plot depicting adsorption of enflurane within the pores of compound (1) in accordance with an embodiment of this invention.
Figure 4:
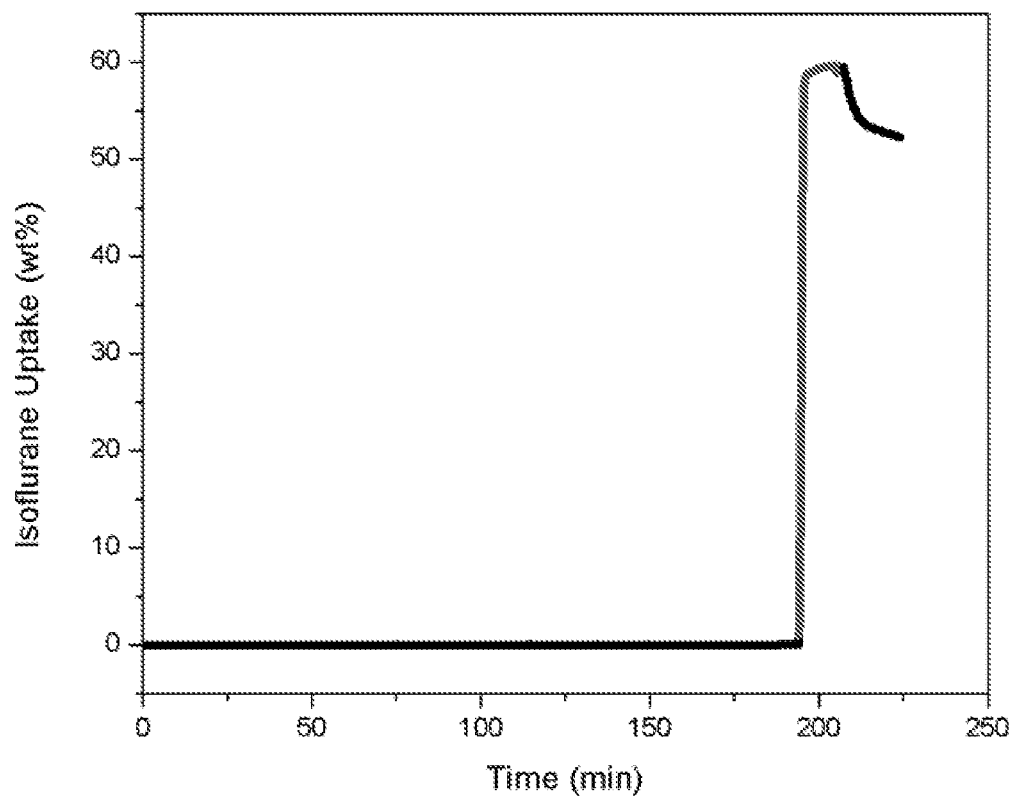
FIG. 4: is a plot depicting adsorption of isoflurane within the pores of compound (1) in accordance with an embodiment of this invention.
Figure 5:
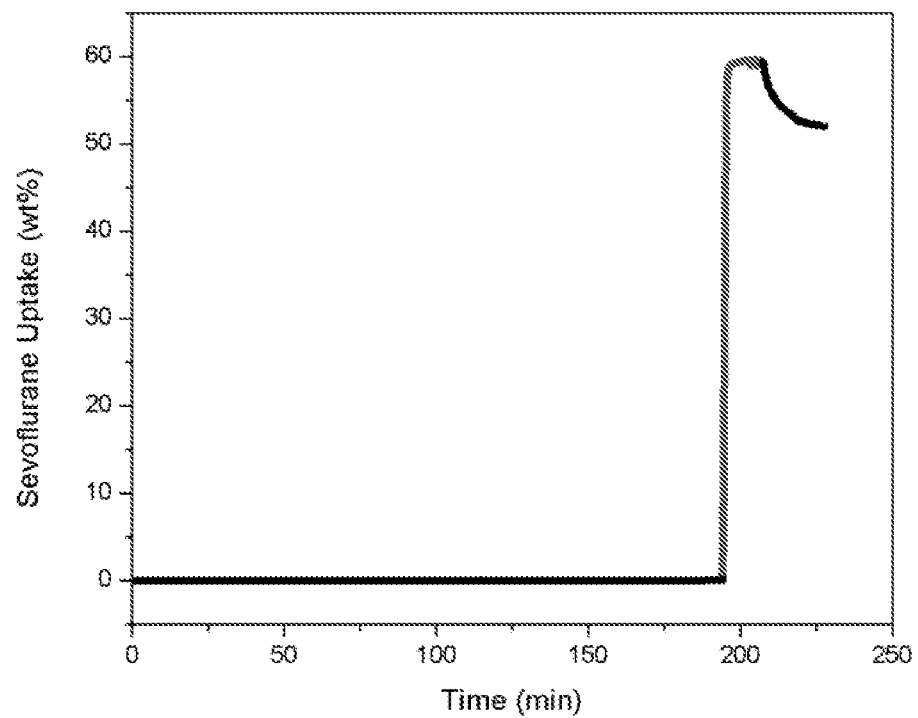
FIG. 5: is a plot depicting adsorption of sevoflurane within the pores of Compound 1 in accordance with an embodiment of this invention.
Figure 6:
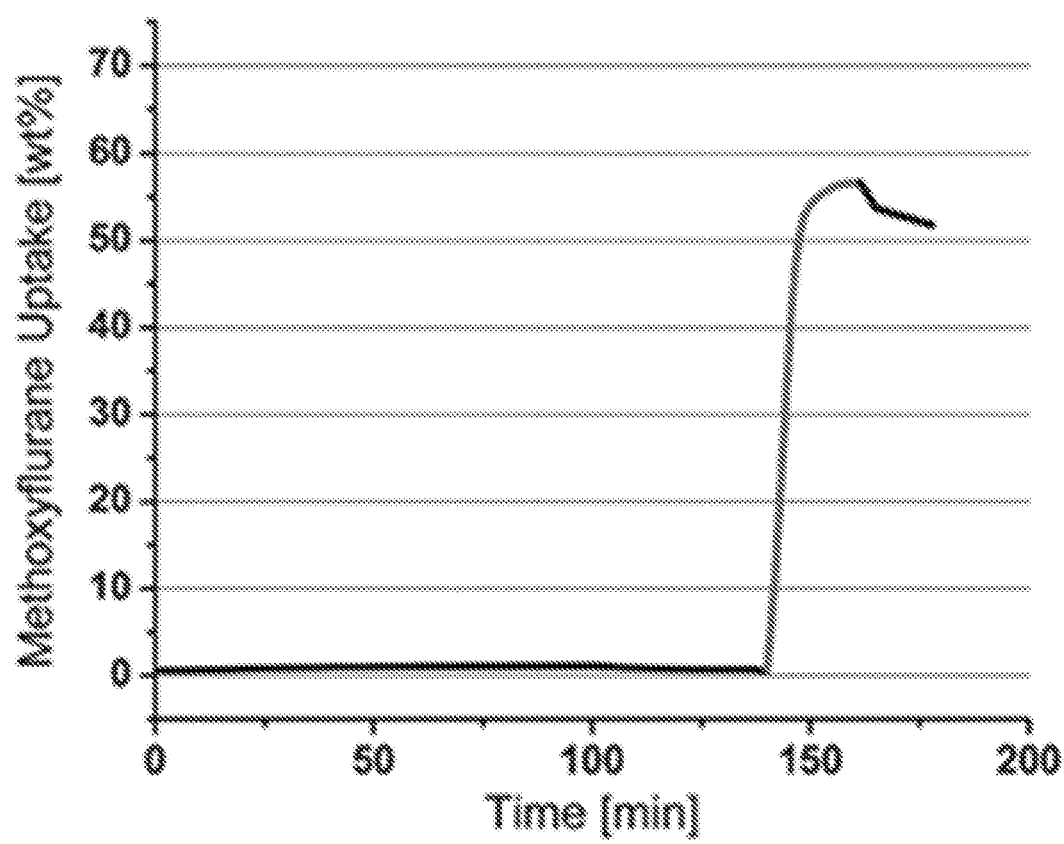
FIG. 6: is a plot depicting adsorption of methoxyflurane within the pores of Compound 1 in accordance with an embodiment of this invention.
Figure 7:
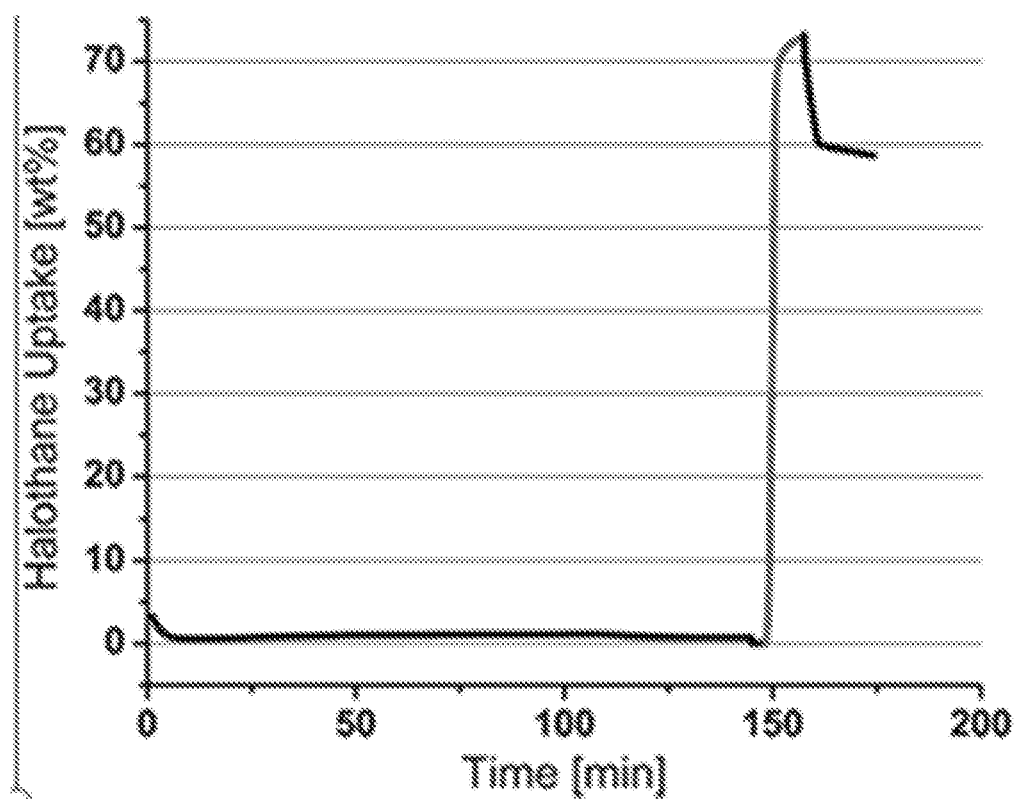
FIG. 7: is a plot depicting adsorption of halothane within the pores of Compound 1 in accordance with an embodiment of this invention.

In some embodiments, quantification of adsorption was performed using thermogravimetric analysis (TGA) wherein crystals of compound 1 were placed into the thermogravimetric balance and first heated to 120° C. (temperature program as depicted in FIG. 2(B)), and maintained at that temperature for 1 h, thereby removing residual solvent and/or volatile guest molecules from the pores of compound 1. The heating was then discontinued and the material was allowed to cool. After the balance reached 25° C. (after approx. 1 h), the flow of carrier gas was switched from pure nitrogen to nitrogen that was allowed to pass over a bubbler reservoir containing the liquid anesthetic of interest. Using embodiments of this methodology, uptake capacities for five fluorinated anesthetics where determined (Table 1).

As described above, in some embodiments, crystals of compound (1) were first heated to 120° C. and kept at that temperature for 1-2 hours. During that time, crystals were in the stream of pure dry nitrogen carrier gas (black curve (linear section of the graph, and section that follows the predominantly vertical component in FIGS. 3-7). After the heating was discontinued and the crystals cooled down to room temperature, the carrier gas was switched to nitrogen enriched with the vapors of a fluorinated anesthetic. This enrichment was performed by passing the nitrogen gas through a bubbler containing the liquid sample of the appropriate anesthetic. This flow of anesthetic-enriched nitrogen is shown by the predominantly vertical component of the curve in FIGS. 3-7.

For all of the examined samples, molar ratios suggested that between two and three molecules of an anesthetic may be captured per molecule of compound 1. In some embodiments the increase in mass is rapid and the fluorinated anesthetic gases are shown to be retained in the pores of compound (1) when flow is switched back to nitrogen gas (second black curve). I.e., once the flow of carrier gas is switched from pure nitrogen (horizontal component of curves in FIG. 3-7) to anesthetic enriched nitrogen (vertical component of curves in FIG. 3-7), adsorbed amount within the porous crystals of compound 1 increases from 1% to 90% of saturation values in: 130 s for enflurane, 72 s for isoflurane, 75 s for sevoflurane, and 130 s for halothane. With methoxyflurane, more than 7 minutes (461 s) were needed to reach 90% saturation. Hence, except in the case of methoxyflurane) uptake of anesthetics by compound 1, were fast.

TABLE 1

Adsorption parameters for embodiments of fluorinated anesthetics within the pores of 1.

| Guest species | Molecular weight (g/mol) | Boiling point [° C.] | Adsorption in (1) | | Desorption temp. [° C.] |
|---|---|---|---|---|---|
| | | | Weight %[a] | In moles, per mole of 1[b] | |
| Enflurane | 184.5 | 56.5 | 59.3 (59.0) | 2.31 | 57 |
| Isoflurane | 184.5 | 48.5 | 59.7 (59.8) | 2.33 | 60 |
| Sevoflurane | 200.1 | 58.6 | 59.6 (59.4) | 2.14 | 63 |
| Methoxy-flurane | 165.0 | 104.8 | 56.7 (56.4) | 2.47 | 83 |
| Halothane | 197.4 | 50.2 | 73.4 (73.6) | 2.67 | 55 |

[a]Values in parenthesis indicate weight adsorption capacities observed in the second attempt.
[b]Molar values were calculated using weight adsorption data from the first attempt.

The disclosure herein provided methods of binding an anesthetic agent within a non-covalent organic framework comprising a compound of Formula (1), wherein the compound forms a porous macrostructure; and adsorbing the anesthetic agent within the pores of the structure formed from a compound exemplified by that of Formula (1). In another embodiment method further comprises delivering an anesthetic agent to a patient in need thereof by virtue of a compound exemplified by Formula (1), wherein the anesthetic agent is bound within the pores of the assembled macro or super structure. A method is also provided wherein the compound sequesters the anesthetic agent from a patient in need thereof, post operatively, or during an operative procedure, and thereby provides a method of reducing toxicity, and post-operative stress, which in some embodiments has particular applicability in pediatric anesthesia. While exemplary embodiments have been shown and described, modifications thereof can be made by one skilled in the art without departing from the scope or teachings herein.

The embodiments describe herein are exemplary only and are not limiting. Many variations and modifications of the systems, apparatus, and processes described herein are possible and are within the scope of the invention as claimed below. Accordingly, the scope of protection is not limited to the embodiments described herein, but is only limited by the claims that follow, the scope of which shall include all equivalents of the subject matter of the claims.

What is claimed is:

1. A method of binding an anesthetic agent comprising:
 contacting a gas comprising an anesthetic agent with a non-covalent organic framework comprising a compound of:

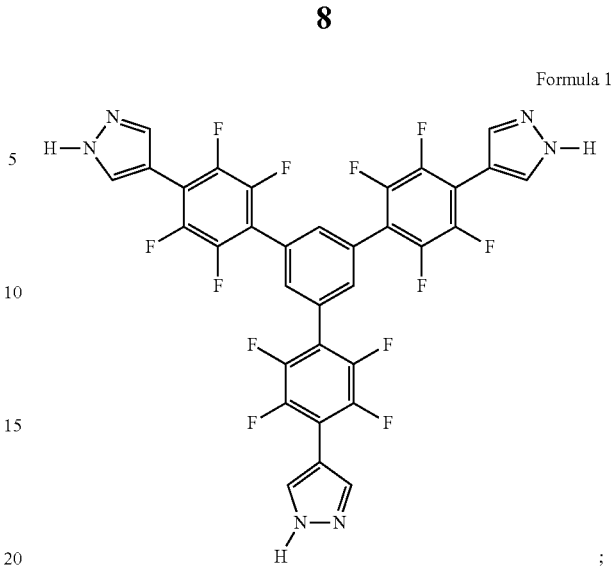

Formula 1 wherein said compound forms a porous supramolecular structure; and
 adsorbing said anesthetic agent within the pores of a compound of Formula 1.

2. The method of claim 1, further comprising delivering said anesthetic agent to a patient in need thereof.

3. The method of claim 2, further comprising sequestering said anesthetic agent from a said patient.

4. The method of claim 3, wherein said sequestering occurs post operatively.

5. The method of claim 3, wherein said sequestering occurs during an operative procedure.

6. The method of claim 3, wherein said sequestering reduces toxicity.

7. The method of claim 3 wherein said sequestering reduces post-operative stress.

8. The method of claim 1, wherein said framework has a weight adsorption capacity of about 50% to about 75% for said anesthetic agent.

9. The method of claim 1, wherein said framework has a weight adsorption capacity of about 60 to about 65% for said anesthetic agent.

10. The method of claim 5, wherein said anesthetic agents comprise fluorinated anesthetics, non-fluorinated anesthetics or a combination thereof.

11. The method of claim 1, wherein the anesthetics comprise sevoflurane, enflurane, isoflurane, methoxyflurane, desflurane, halothane, or combinations thereof.

* * * * *